US006418803B1

(12) United States Patent
Billman

(10) Patent No.: US 6,418,803 B1
(45) Date of Patent: Jul. 16, 2002

(54) METHOD FOR TESTING THE EFFECTIVENESS OF DRAIN CLEANERS

(75) Inventor: Fred F. Billman, Racine, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

(21) Appl. No.: 09/353,473

(22) Filed: Jul. 13, 1999

(51) Int. Cl.[7] ............................................... G01N 19/00
(52) U.S. Cl. ...................................................... 73/865.9
(58) Field of Search ...................... 510/195; 134/22.13; 73/365.9

(56) References Cited

U.S. PATENT DOCUMENTS

| 2,486,246 A | | 10/1949 | Beeke ............................ 4/199 |
| 3,503,890 A | * | 3/1970 | Davisson et al. ............ 252/152 |
| 3,875,083 A | * | 4/1975 | Murtaugh .................... 252/535 |
| 4,060,494 A | * | 11/1977 | Schoenholz et al. ......... 252/105 |
| 4,664,836 A | * | 5/1987 | Taylor, Jr. et al. ............. 252/91 |
| 5,624,891 A | * | 4/1997 | Smialowicz et al. ......... 510/195 |
| 5,630,883 A | | 5/1997 | Steer et al. ............... 134/22.13 |
| 5,783,537 A | * | 7/1998 | Ahmed et al. ............... 510/193 |
| 6,136,768 A | * | 10/2000 | Dawson et al. ............. 510/195 |

OTHER PUBLICATIONS

C. Potera, 273 Science 1795–97 "Biolfilms Invade Microbiology" (1996).
J. W. Costerton, 15 J. Ind. Microb 137–140 "Overview of Microbial Biofilms" (1998).
Letter from S.C. Johnson & Son, Inc. to National Broadcasting Company dated Oct. 10, 1997 regarding Advertising for "Drano Max" brand drain clog remover.

* cited by examiner

Primary Examiner—Hezron Williams
Assistant Examiner—C D Garber

(57) ABSTRACT

Disclosed herein are methods. for testing the effectiveness of drain cleaners. A model drain is provided with removable sections, two of which have structures for mounting representative clogs. Flow rates are monitored as chemical drain cleaner is applied, and after rinsing. Residual clog can also be measured.

10 Claims, 3 Drawing Sheets

METHOD FOR TESTING THE EFFECTIVENESS OF DRAIN CLEANERS

CROSS REFERENCES TO RELATED APPLICATIONS

Not applicable.

STATEMENT REGARDING FEDERALLY SPONSORED RESEARCH

Not applicable.

BACKGROUND OF THE INVENTION

The present invention relates to methods for testing the effectiveness of drain cleaners on clogs commonly experienced in plumbing drains.

Most plumbing drains have a vertical entry which extends directly or indirectly into a U-shaped section that is referred to as a "trap". Liquid typically remains in the trap at all times, thereby preventing sewer gases from returning up into the building through the drain (hence the gases are trapped). Downstream of the trap are one or more laterals and connectors that ultimately link the drain to the sewer system.

Drains for bathroom sinks and certain bathtubs often have a pop-up type valve mounted in their vertical entry. Kitchen sinks often have their vertical entry covered by a removable strainer. Other bathtubs have screens or stoppers covering their drain entry.

Given these obstructions, and that piping is usually a non-transparent metal or plastic, it is difficult for a consumer (or even a plumber) to know what is causing a particular clog, much less exactly where the clog is. The art had believed that hair was the primary cause of household clogs. This is in part because removal of the pop-up valve or other valve structure often disclosed wads of hair tangled around the valve. However, much less was known about where downstream clogs form, and what they are formed from.

It has therefore been difficult to optimize or completely evaluate drain cleaners. Potential drain cleaners have typically been tested in a laboratory by how quickly they dissolved hair in a container (see e.g. U.S. Pat. No. 5,630,883). The disclosure of this patent, and of all other publications referred to herein, are incorporated by reference as if fully set forth herein. While this technique has value, the value is limited to particular types of clogs.

Consumer feedback is of only limited value with respect to drain,cleaner effectiveness. When a clog is successfully chemically dissolved by a consumer, it is seldom clear where the clog was, how serious it was, and what it was made of. When a chemical drain cleaner fails to remove the clog, a plumber is usually called in to dislodge the clog using a plumber's snake or other equipment. The dislodged clog is usually washed into the sewer system, with the result that essentially nothing is learned about why the chemical drain cleaner failed.

Complicating matters is the fact that parts of many drain assemblies (especially those extending from bathtubs) are for, all practical purposes inaccessible (except through the drain inlet) once the building has been constructed. Even when the trap area and some downstream connectors are accessible (as is typical for a kitchen sink), the piping is typically made of plastic or metal so that the nature and placement of the clog cannot be easily determined.

Another problem is the reluctance of certain regulatory authorities to permit certain types of comparative advertising claims in the absence of more representative scientific experiments. Thus, consumers have not been able to receive sufficiently detailed comparative information relevant to the effectiveness of drain cleaners in the marketplace.

Thus a need exists for improved methods for testing chemical drain cleaners.

BRIEF SUMMARY OF THE INVENTION

In one aspect, the invention provides a method for testing a chemical drain cleaner. One obtains a test drain having a vertical entry, a trap extending downstream from the vertical entry, a lateral extending downstream from the trap, and mounting means in at least one of the vertical entry and the lateral for mounting a test clog.

One positions the test clog in the drain at the mounting means. One then adds a chemical drain cleaner to the drain through the vertical entry. Thereafter, one pours rinse fluid (usually water) into the vertical entry. One then measures the amount of residual test clog left in the drain or the flow rate through the drain after the treatment. In an alternative form, the test clog is made of hair and the trap is u-shaped.

If desired, the hair can be coated in a polysaccharide to simulate some of the effects of biofilm on drain clogs. Alternatively, hair coated with naturally formed biofilm can be used in the test drain.

The method can test a wide variety of cleaners such as those containing caustic materials such as sodium hydroxide, mixtures of sodium hydroxide, metal (e.g. aluminum) chips, and sodium nitrate, or alkaline sodium hypochlorite solutions (e.g. U.S. Pat. No. 4,080,305), as well as other cleaners such as those with additives such as surfactants, proteolytic enzymes, and disulfide reducing agents. See e.g. U.S. Pat. Nos. 4,540,506, 4,619,710 and 3,503,890.

By the term "chemical drain cleaner" I mean any liquid or solid material, other than water or water from a plumbing supply (e.g. softened water; hard water), which is being tested for use (or used or marketed for use) to remove drain clogs and/or to, protect against drain clogs. Thus, laundry bleach would be deemed to be a chemical drain cleaner when tested or used for drain cleaning, or earlier when that bleach was actually marketed for that purpose.

The mounting means is preferably the radially inwardly projecting stem of a pop-up valve (or other bar that can be radially inserted through a side wall of the vertical entry or lateral). It is preferably positioned at a point in the drain having a diameter of about 2.0 to 5.0 cm. One example is the assembly of FIG. 1 of U.S. Pat. No. 2,486,246 (stem end 26).

The parts of the drain (e.g. the lateral and trap) are designed to be uncoupled (by threading) from the trap (e.g. to provide access to the mounting means downstream of the trap).

In another form, the flow rate is monitored after the drain cleaner is added until the rinse water is added. This provides information regarding how long the drain cleaner adheres to the drain and drain contents.

Rinse water flow rates can also be monitored. The rinse water is preferably tested at selected intervals to determine drain cleaner content. This is preferably done by emptying the trap prior to rinsing. This technique permits an evaluation of the adherence of the drain cleaner to the clog.

In an alternative embodiment, such a drain is provided.

The objects of the present invention therefore include providing methods of the above kind:

(a) that permit the evaluation of drain cleaners;

(b) which permit drain cleaners to be developed that have improved effectiveness for particular types of clogs; and (c) which evaluate comparative effectiveness of drain cleaners.

These and still other objects and advantages of the present invention (e.g. providing the drains) will be apparent from the description which follows. The following description is merely of the preferred embodiments. Thus, the claims should be looked to in order to understand the full scope of the invention.

DETAILED DESCRIPTION

Clog Evaluation

I examined clogged drains reported by consumers. A borescope with video recording capability was inserted into the clogged drains. I used the camera of the borescope to identify the position and nature of the clogs.

Apart from the occasional large physical object caught in the trap (e.g. a small toy), most household clogs were found to be due to hair and/or biofilm. See generally C. Potera, 273 Science 1795–1797 (1996) (general discussion of biofilms). Grease and soap rarely were significant clog factors.

Bacteria secrete polysaccharide which helps anchor them in moving water in drains. This provides a home and encasement for the bacteria which is very sticky. This biofilm in turn traps particles.

About 30% of the clogs were found in the vertical entry. These were usually due to hair tangling on pop-up/control valves. Only about 5% of the clogs were found in the trap. About 30% of the clogs were found in a lateral extending, from the trap. These were usually biofilm based, sometimes also with hair. The rest of the clogs were further downstream. These typically also involved primarily biofilm.

Model Drain

Figure 1:
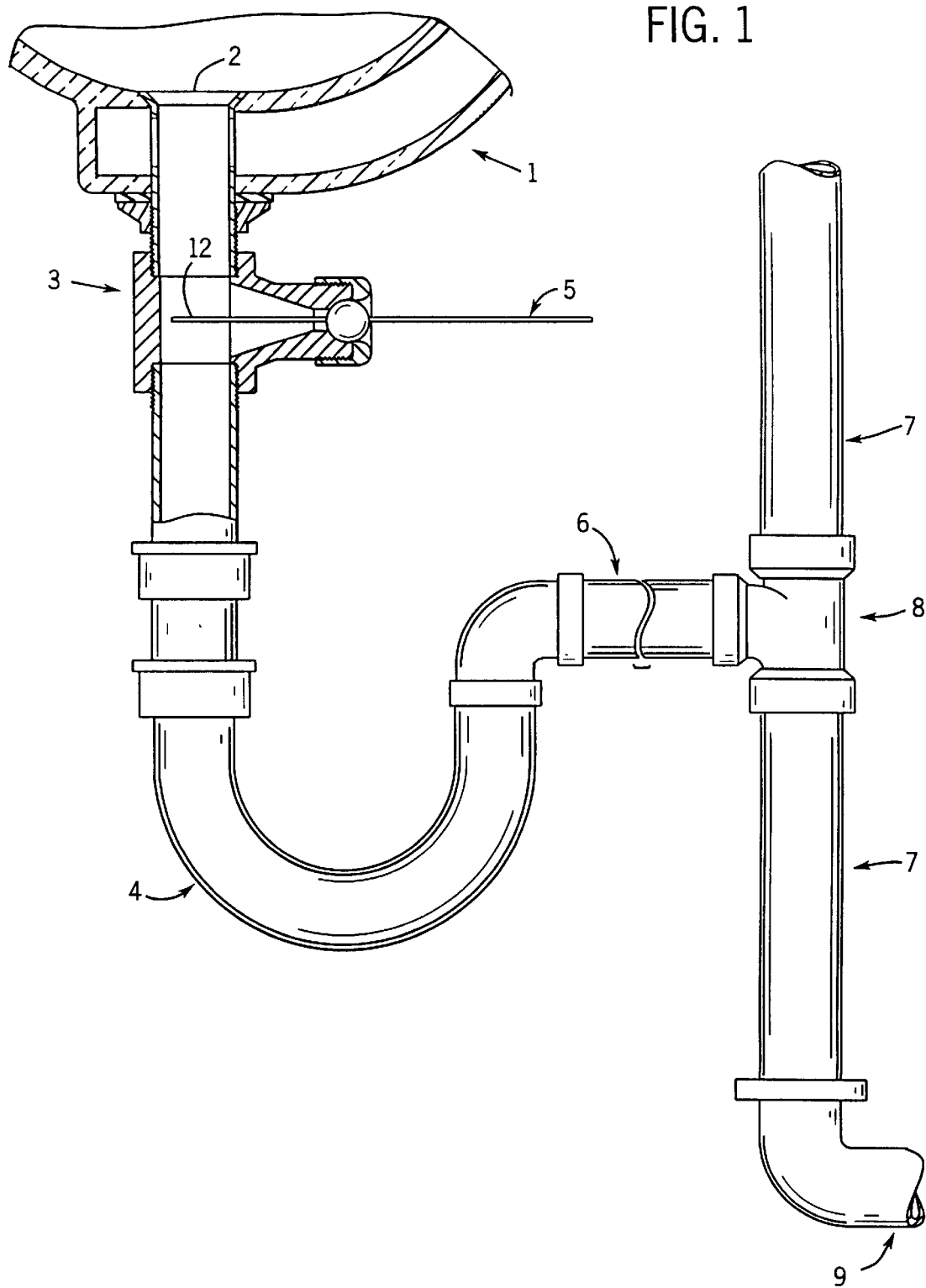
FIG. 1 is a sketch of a test model system in elevational view.

FIG. 1 shows my preferred model drain. It has a basin 1, an entry throat 2, a vertical entry 3, a trap 4, a pop-up control. stem 5, a lateral 6, a further vertical pipe 7, a t-joint 8, and an exit lateral 9. Each of these segments are of a size typical for a bathroom sink. Segments are removably threaded to each other.

Hair wads or hair balls can be placed at any location in the drain system by cutting or separating the pipe at the desired location and placing fine nylon mesh between the separated pipe sections. The pipes are reconnected by means of rubber tubing connectors (available at Hardware Stores). Clamps hold the rubber tubing connectors and the fine nylon mesh securely to the pipes. The nylon mesh holds the hair wads or hair balls in place.

Testing

To test a drain cleaner, a folded swatch in the vertical entry (or a hairball in the lateral) can be clipped to a stem 12. A single clog can be tested at a time, or both clogs can be tried simultaneously.

A specific amount of drain cleaner is poured into the throat. After a waiting time (typically 15 minutes to overnight), the system is rinsed with a standard amount of water. Flow rates are monitored before and after rinsing. Rinse water is also analyzed for drain cleaner content at various times.

Specific Comparative Test

The drain cleaners that were used for this test were purchased from stores and were checked for code dates so that the products showed similar ages. At the selected typical shelf life, Drano® Max(red bottle) initially containing 7.0% bleach had decomposed to 5.2–5.8% bleach while the Liquid Plumber® (gray bottle) had decomposed from the initial concentration of 5.8% bleach to 4.8–5.3%.

Standard European virgin brown hair 14 (10 inches long) was purchased from Demeo Brothers (N.Y.). Twenty-seven and five tenths grams of this hair was tied in the middle with a small piece of string and folded in half and secured with a colored plastic cable tie 15. The hair was then trimmed to 5.5". The tie was placed as close to the top of the fold as possible (¾" from the top) with the majority of the hair: hanging loosely beneath the tie. The weight of this trimmed 5.5" dry swatch with the plastic tie was recorded as the "before" weight. This trimmed hair and plastic tie usually weighed 22.5 to 27.5 g.

Hair swatches cut as explained above were then added to a 1% aqueous Agree shampoo system (shampoo is to help the hair hydrate faster). After soaking in this solution for 1 hour the hydrated hair (which swells when hydrated) was removed, immediately patted dry with paper towels to remove surface moisture from the hydrated hair. A soap solution was made up by dissolving 1.35 g of grated Ivory Soap (tallow soap) in 10 ml of boiling water. This solution was swirled and kept hot in order to keep all the soap dissolved. The patted dry hair is then immersed into the 10 ml of hot dissolved soap solution such that all of the solution is absorbed onto the hair.

The hair swatch is then held upside down and the wet soapy hair massaged such that the soap uniformly coats the hair swatch. Being held upside down prevents soap solution from dripping off the wet cut end. The hair swatch is then hung to dry for 2 hours immediately before use at a humidity of 40 to 58% to allow some of the moisture to leave the soap solution and thus allow the soap to become more firmly attached to the hair. Just before placing it in the drain the hair is soapy and still slightly moist.

Figure 2:
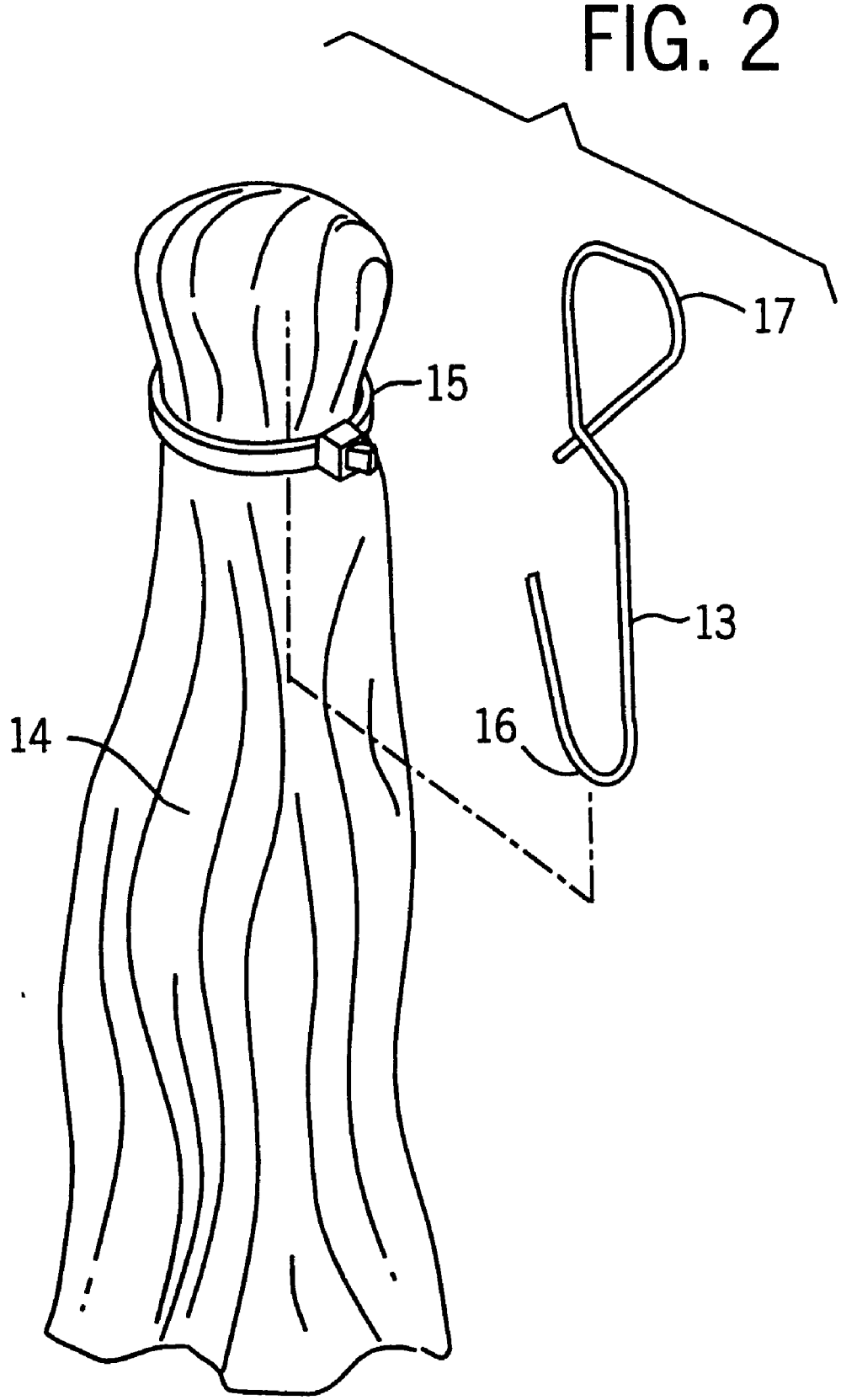
FIG. 2 is a perspective view of an example hair "clog" and attachment clip.
Figure 3:
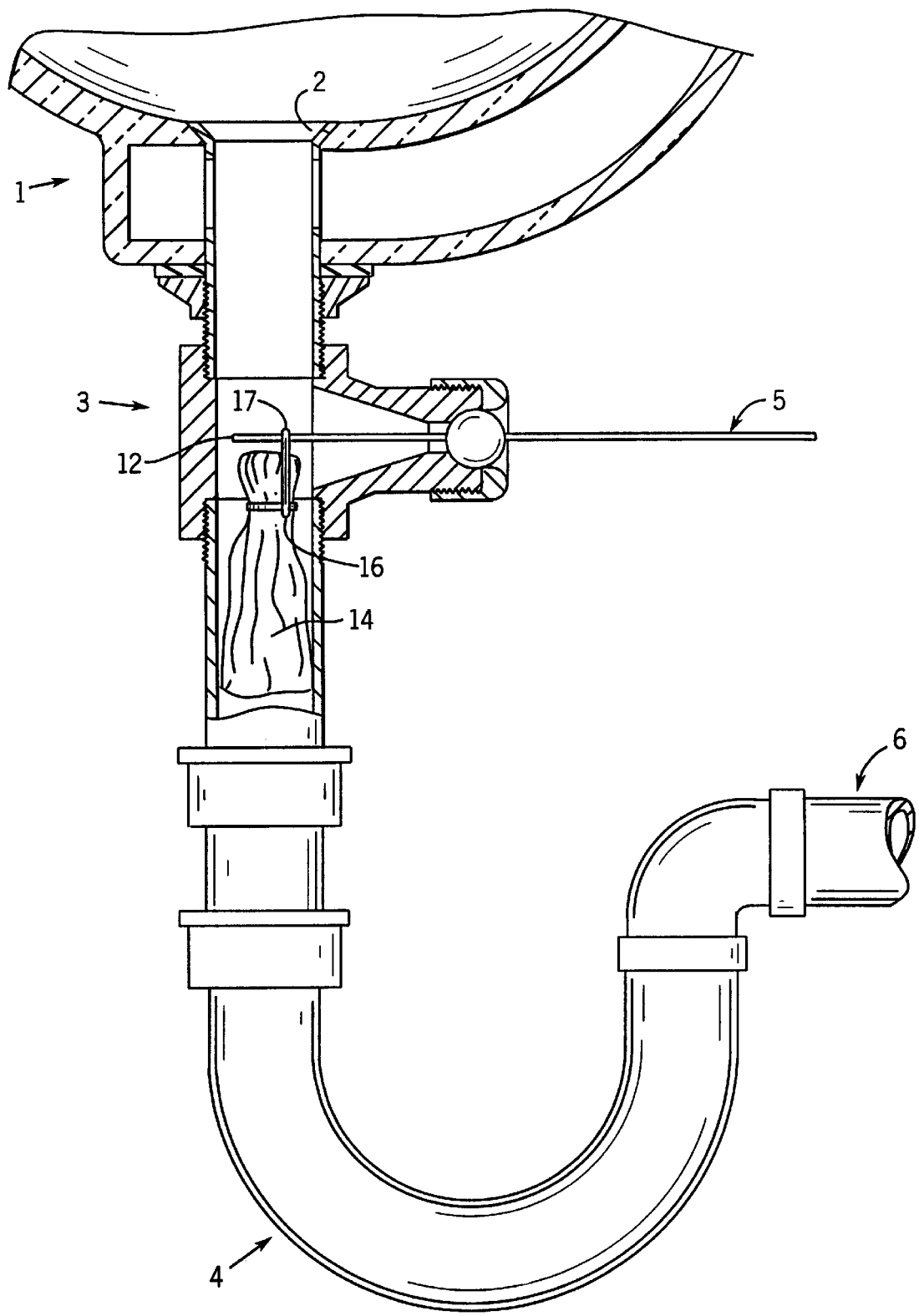
FIG. 3 is an enlarged sectional view of a portion of the FIG. 1 model system, but with the clog shown.

As will best be appreciated from FIG. 2, these hair swatches can be attached to the drain opening/closing rod stem 12 in the sink throat by means of a plastic clip 13 opened up such that one end 16 of the clip can be pushed under the plastic tie in the hair and the larger end can be looped 17 above the top of the hair swatch so that the rod opening/closing stem 12 can be inserted through to hold the swatch in the throat (see FIG. 3). Thus the hair is suspended by means of a clip attached at one end to the hair swatch and the other to the drain control rod mechanism.

Usually six or more soapy hair swatches are made up. If not used immediately, they are stored in a 95% humidity chamber to prevent drying. Preferred tests are side-by-side tests with matching initial flow rates. Thus, swatches are first tested in the sink drain system to determine their flow rates. We select hair swatches that provide similar flow rates.

Two hair swatches treated as aforementioned and closely matched by flow rate are then placed in the throats of two side by side sinks. These are then checked for a final time for flow rate by running seven flow rate tests of one gallon of 80F water. It is important that flow rates show a stable pattern.

Once the flow rates have stabilized and five good sequential readings have been obtained for both clogs, the test begins. The drain is set up so that the bottom of the hair hanging in the vertical throat does not touch the water/product in the trap when the trap is full.

The drain flow rates are done by pouring one gallon of 80 degree Fahrenheit water into a stoppered sink. The stopper is removed and the time for the sink to drain to the stoppered drain entrance is measured. Then five hundred grams of drain cleaner are poured directly into the drain. Product is measured for bleach content immediately before use.

The product is then allowed to drain for fifteen minutes. During this time the volume of product coming out the end of the pipe is recorded at regular time intervals starting at a 30 seconds. Several readings less than five minutes are obtained, then 5 minute, 10 minute and finally the 15 minute flow rate readings are taken and recorded. Drano® Max and Liquid Plumber® tests were run side by side so that timed measurements of the liquid exiting the system could be recorded simultaneously.

After fifteen minutes the trap was then disconnected, emptied into a 1500 ml beaker, replaced and the system rinsed with 1000 ml of deionized water. This rinse was collected in the same beaker holding the trap residue and analyzed for bleach content. This tested viscosity of the drain cleaner without interference from the fact that drain cleaner tends to remain in the trap.

The drain was then rinsed with two gallons of 120 degree Fahrenheit water. Then the flow rate of the drain was taken again by the same one gallon method as mentioned above. Again seven flow rates are taken and only the last 5 are used to determine the final flow rate.

The hair clogs remnants were then removed and rinsed thoroughly with hot water. The clip was cut along with the string tied in the center and these kept with the hair swatch for identification during all of the rinsing, drying and weighing steps. Different tests used different colors of plastic cable ties which were recorded with their initial hair weights and final hair weights to prevent human error.

The rinsed hair swatches along with the cut plastic cable ties were placed in a 105 degree Fahrenheit forced air oven overnight for drying. Before taking the final weights, the hair swatches were removed from the oven and allowed to equilibrate at room temperature for two days.

If such a series of tests are run there will typically be one drain that flows slightly slower than the other. Thus, products are alternated such that the slowest drain was used for Drano® Max in the first test, the slowest drain in the second test was used for Plumber®.

| Drano® | | | | |
|---|---|---|---|---|
| Flow Rate Data (seconds) | | | | |
| Trial | Initial | Final | Improvement | % Improvement |
| 1 | 91.2 | 30.0 | 61.2 | 67.1 |
| 2 | 117.5 | 90.4 | 27.1 | 23.1 |
| 3 | 158.3 | 53.6 | 104.7 | 66.1 |
| 4 | 123.5 | 84.2 | 39.3 | 31.8 |

-continued

| Drano® | | | | |
|---|---|---|---|---|
| 5 | 118.2 | 71.6 | 46.6 | 39.4 |
| 6 | 101.3 | 51.5 | 49.8 | 49.2 |
| 7 | 124.2 | 56.7 | 67.5 | 54.3 |
| 8 | 103.5 | 40.7 | 62.8 | 60.7 |
| 9 | 160.8 | 44.2 | 116.6 | 72.5 |
| 10 | 103.3 | 44.5 | 58.8 | 56.9 |
| Avg. | 120.2 | 56.7 | 63.4 | 52.8 |
| Hair Dissolution Data (grams) | | | | |
| Trial | Initial Weight | Final Weight | Amt. Dissolved | % Dissolved |
| 1 | 25.70 | 21.42 | 4.28 | 16.65 |
| 2 | 28.13 | 23.78 | 4.35 | 15.46 |
| 3 | 28.30 | 23.49 | 4.81 | 17.00 |
| 4 | 27.40 | 24.78 | 2.62 | 9.56 |
| 5 | 25.90 | 24.41 | 1.49 | 5.75 |
| 6 | 27.07 | 24.81 | 2.26 | 8.35 |
| 7 | 26.47 | 23.42 | 3.05 | 11.52 |
| 8 | 23.81 | 20.91 | 2.90 | 12.18 |
| 9 | 25.90 | 21.25 | 4.65 | 17.95 |
| 10 | 23.54 | 20.56 | 2.98 | 12.66 |
| Avg. | 26.22 | 22.88 | 3.34 | 12.73 |

| Liquid Plumber® | | | | |
|---|---|---|---|---|
| Flow Rate Data (seconds) | | | | |
| Trial | Initial | Final | Improvement | % Improvement |
| 1 | 102.6 | 57.0 | 45.6 | 44.4 |
| 2 | 110.2 | 106.8 | 3.4 | 3.1 |
| 3 | 175.0 | 129.5 | 45.5 | 26.0 |
| 4 | 113.5 | 160.3 | 0.0 | 0.0 |
| 5 | 123.8 | 129.0 | 0.0 | 0.0 |
| 6 | 104.8 | 101.0 | 3.8 | 3.6 |
| 7 | 113.7 | 91.5 | 22.2 | 19.5 |
| 8 | 89.0 | 69.0 | 20.0 | 22.5 |
| 9 | 171.7 | 131.7 | 40.0 | 23.3 |
| 10 | 99.3 | 70.5 | 28.8 | 29.0 |
| Avg. | 120.4 | 104.6 | 20.9 | 17.1 |
| Hair Dissolution Data (grams) | | | | |
| Trial | Initial Weight | Final Weight | Amt. Dissolved | % Dissolved |
| 1 | 25.77 | 24.62 | 1.15 | 4.46 |
| 2 | 24.70 | 24.20 | 0.50 | 2.02 |
| 3 | 29.50 | 28.97 | 0.53 | 1.80 |
| 4 | 27.08 | 26.88 | 0.20 | 0.74 |
| 5 | 27.22 | 27.17 | 0.05 | 0.18 |
| 6 | 27.18 | 26.56 | 0.62 | 2.28 |
| 7 | 26.43 | 26.09 | 0.34 | 1.29 |
| 8 | 23.53 | 23.49 | 0.04 | 0.17 |
| 9 | 22.96 | 22.18 | 0.78 | 3.40 |
| 10 | 22.77 | 22.43 | 0.34 | 1.49 |
| Avg. | 25.71 | 25.26 | 0.46 | 1.77 |

Tests using this drain have, among other things, already permitted me to improve rinsing protocols for a liquid drain cleaner. I expect it to also be beneficial in many other ways in connection with developing and improving drain cleaners, and evaluating comparative attributes.

It will be appreciated that the above describes only a preferred embodiment of the invention. In this regard, the hair can be dipped into a polysaccharide bath, and then positioned in the lateral. This simulates hair with biofilm on it. This permits more representative studies relating to the effectiveness of the cleaner on downstream clogs. Instead of swatches being used, balled-up hair or wadded hair can be used.

Alternatively, the hair clogs can be inserted into a normally utilized sink with the sink being used until real biofilm forms on the clog. The clog can then be used in the model drain. However, this provides somewhat less consistency with respect to the nature of the clog.

Hair without soap can be used in these tests and gives the same win-lose test results for any two products tested as would soapy hair.

As such, the claims should be looked to in order to judge the full scope of protection.

Industrial Applicability

The invention provides methods for testing the effectiveness of chemical drain cleaners, as well as model drains for use in such tests.

What is claimed is:

1. A method for testing a chemical drain cleaner, comprising the steps of:
    obtaining a test drain having a vertical entry, a trap extending downstream from the vertical entry, a lateral extending downstream from the trap, and mounting means in at least one of the vertical entry and the lateral for mounting a test clog;
    positioning a test clog in the drain by attaching it to the mounting means;
    then adding a chemical drain cleaner to the drain through the vertical entry; and
    then pouring rinse fluid into the vertical entry; and
    then determining the amount of residual test clog left in the drain or the flow rate through the drain;
    wherein the test clog comprises hair and the determining step involves weighing residual hair that had been left attached to the mounting means in the drain.

2. The method of claim 1, wherein the trap is u-shaped and the clog also comprises a polysaccharide.

3. The method of claim 1, wherein the rinse fluid is water.

4. The method of claim 1, wherein the chemical drain cleaner is a liquid.

5. The method of claim 1, wherein the chemical drain cleaner is a caustic drain cleaner.

6. The method of claim 1, wherein the chemical drain cleaner comprises a hypocholorite.

7. The method of claim 1, wherein the lateral is suitable to be uncoupled from the trap to provide access to a mounting means in the lateral.

8. The method of claim 1, wherein a flow rate of rinse fluid through the drain is measured after rinse fluid is poured into the vertical entry.

9. A method for testing a chemical drain cleaner, comprising the steps of:
    obtaining a test drain having a vertical entry, a trap extending downstream from the vertical entry, a lateral extending downstream from the trap, and mounting means in at least one of the vertical entry and the lateral for mounting a test clog;
    positioning a test clog in the drain by attaching it to the mounting means;
    then adding a chemical drain cleaner to the drain through the vertical entry; and
    then pouring rinse fluid into the vertical entry; and
    then determining the amount of residual test clog left in the drain or the flow rate through the drain,
    wherein the rinse fluid is not poured into the vertical entry until after a delay period of at least 10 minutes after the chemical drain cleaner has been added and a flow rate through the drain is measured during that delay period.

10. A method for testing a chemical drain cleaner, comprising the steps of:
    obtaining a test drain having a vertical entry, a trap extending downstream from the vertical entry, a lateral extending downstream from the trap, and mounting means in at least one of the vertical entry and the lateral for mounting a test clog;
    positioning a test clog in the drain by attaching it to the mounting means;
    then adding a chemical drain cleaner to the drain through the vertical entry; and
    then pouring rinse fluid into the vertical entry; and then determining the amount of residual test clog left in the drain or the flow rate through the drain,
    wherein the trap is emptied after the drain cleaner is added and before the rinse water is added, and rinse water exiting the drain is tested to determine concentration of dissolved chemical drain cleaner in exiting rinse fluid.

* * * * *